(12) United States Patent
Carbo et al.

(10) Patent No.: US 8,997,579 B2
(45) Date of Patent: Apr. 7, 2015

(54) MOUNT ASSEMBLY FOR COMPRESSION TESTING OF PROTECTIVE ARTICLES OF APPAREL

(75) Inventors: Jorge E. Carbo, Aloha, OR (US); Martine I. V. Mientjes, Beaverton, OR (US); Jeffrey D. Allison, Lake Oswego, OR (US)

(73) Assignee: NIKE, Inc., Beaverton, OR (US)

( * ) Notice: Subject to any disclaimer, the term of this patent is extended or adjusted under 35 U.S.C. 154(b) by 201 days.

(21) Appl. No.: 13/604,433

(22) Filed: Sep. 5, 2012

(65) Prior Publication Data

US 2014/0060202 A1    Mar. 6, 2014

(51) Int. Cl.
| | |
|---|---|
| *G01L 1/00* | (2006.01) |
| *G01L 1/22* | (2006.01) |
| *A41D 13/00* | (2006.01) |
| *G01M 7/08* | (2006.01) |
| *G01N 3/30* | (2006.01) |
| *G01N 33/00* | (2006.01) |

(52) U.S. Cl.
CPC .............. *G01L 1/2206* (2013.01); *A41D 13/00* (2013.01); *G01M 7/08* (2013.01); *G01N 3/30* (2013.01); *G01N 2033/008* (2013.01); *G01N 2203/0005* (2013.01); *G01N 2203/001* (2013.01); *G01N 2203/0019* (2013.01); *G01N 2203/0246* (2013.01)

(58) Field of Classification Search
CPC ........ G01L 1/005; G01L 1/2206; G01B 7/16; G01G 19/12
USPC ............................................ 73/760, 855, 856
See application file for complete search history.

(56) References Cited

U.S. PATENT DOCUMENTS

| | | | |
|---|---|---|---|
| 3,557,471 A | 1/1971 | Payne et al. | |
| 3,755,920 A | 9/1973 | Smrcka | |
| 4,349,339 A | 9/1982 | Daniel | |
| 4,850,877 A | 7/1989 | Mason et al. | |
| 5,716,302 A | 2/1998 | Andersson | |
| 5,850,033 A | 12/1998 | Mirzeabasov et al. | |
| 6,833,924 B2 | 12/2004 | Love et al. | |
| 6,923,081 B2 | 8/2005 | Krstic | |
| 6,986,290 B2 | 1/2006 | Konosu | |
| 7,509,835 B2 * | 3/2009 | Beck | 73/12.01 |
| 7,800,505 B2 * | 9/2010 | Pietersen | 340/573.1 |
| 7,930,920 B2 | 4/2011 | Le Carpentier | |
| 2005/0137462 A1 * | 6/2005 | Cho | 600/300 |
| 2007/0160966 A1 | 7/2007 | Cohen et al. | |

OTHER PUBLICATIONS

The successful supply of PPE—an essential guide; http://www.satrappeguide.com/EN1621.php; accessed on Nov. 12, 2013.

(Continued)

*Primary Examiner* — Max Noori
(74) *Attorney, Agent, or Firm* — Shook, Hardy & Bacon L.L.P.

(57) ABSTRACT

A mount assembly for compression testing of an article of apparel on a compression testing machine. The machine has a head and a sensor. The mount assembly includes a substantially rigid core member and a resilient member that is supported on and that at least partially covers the cover member. The resilient member is configured to support the article of apparel thereon. The resilient member is configured to resiliently deform in response to a compression applied to the article of apparel from the head of the impact testing machine. As such, the sensor detects an effect of the compression on at least one of the resilient member and the core member.

17 Claims, 3 Drawing Sheets

(56) References Cited

OTHER PUBLICATIONS

Test Method and Standard Performance Specification for Newly Manufactured Soccer Shin Guards, prepared by National Operating Committee on Standards for Athletic Equipment, accessed Jul. 16, 2012 at: http://www.nocsae.org/standards/pdfs/ND090-06m07-%20Mfr'd%20Soccer%20Shin%20Guards%20Std%20performance.pdf.

* cited by examiner

MOUNT ASSEMBLY FOR COMPRESSION TESTING OF PROTECTIVE ARTICLES OF APPAREL

FIELD

The present disclosure relates to compression testing and, more particularly, to a mount assembly for compression testing of protective articles of apparel.

BACKGROUND

This section provides background information related to the present disclosure which is not necessarily prior art.

Athletes often wear protective pads, guards, masks, and other protective articles of apparel. For instance, American football players often wear thigh guards that are worn to protect the player's thighs. As such, the thigh area can be protected from contusions or other injuries that could otherwise occur during play.

These articles of apparel can be tested on a compression testing machine, such as an impact testing machine. These tests can reveal the compressive strength of the apparel, the impact strength of the apparel, or other characteristics of the apparel. This data can be used to evaluate the suitability of the apparel for protecting a wearer during use.

SUMMARY

This section provides a general summary of the disclosure, and is not a comprehensive disclosure of its full scope or all of its features.

A mount assembly for compression testing of an article of apparel on a compression testing machine is disclosed. The machine has a head and a sensor. The mount assembly includes a substantially rigid core member and a resilient member that is supported on and that at least partially covers the cover member. The resilient member is configured to support the article of apparel thereon. The resilient member is configured to resiliently deform in response to a compression applied to the article of apparel from the head of the impact testing machine. As such, the sensor detects an effect of the compression on at least one of the resilient member and the core member.

Also, a method of compression testing an article of apparel is disclosed. The method includes mounting the article of apparel on a resilient member that is supported by a substantially rigid core member. The method also includes applying a compression to the article of apparel with a head. Additionally, the method includes detecting an effect of the compression on at least one of the resilient member and the rigid core member.

Still further, an artificial thigh for impact testing of a thigh guard on an impact testing machine having an impactor head is disclosed. The artificial thigh includes a single-body resilient member having a main body with a C-shaped cross section and that extends along a straight longitudinal axis. The main body has an outer surface configured to nestingly receive the thigh guard thereon. The main body also has an inner surface. The resilient member additionally includes at least one projection that projects perpendicularly away from the longitudinal axis and away from the main body. Moreover, the resilient member is made from silicone. The resilient member is configured to resiliently deform in response to an impact applied to the thigh guard from the impactor head of the impact testing machine. Additionally, the artificial thigh includes a substantially rigid core member having a D-shaped cross section and that extends along the longitudinal axis. The core member is received by the resilient member to abut against the inner surface of the resilient member and to be at least partially covered by the resilient member. Moreover, the artificial thigh includes a base plate that supports the core member and the resilient member. The base plate is configured to attach to the impact testing machine. Furthermore, the artificial thigh includes a pressure sensor that is configured to be disposed between the thigh guard and the outer surface of the resilient member. The pressure sensor is operable to detect a pressure distribution on the outer surface of the resilient member due to the impact applied to the thigh guard from the impactor head of the impact testing machine.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
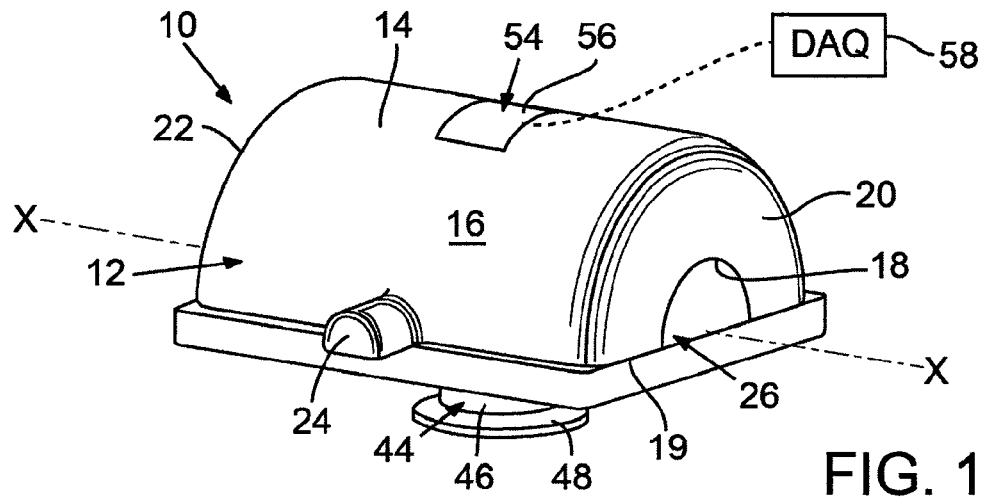
FIG. 1 is a perspective view of a mount assembly used for impact or other compression testing of protective equipment according to various exemplary embodiments of the present disclosure.
Figure 2:
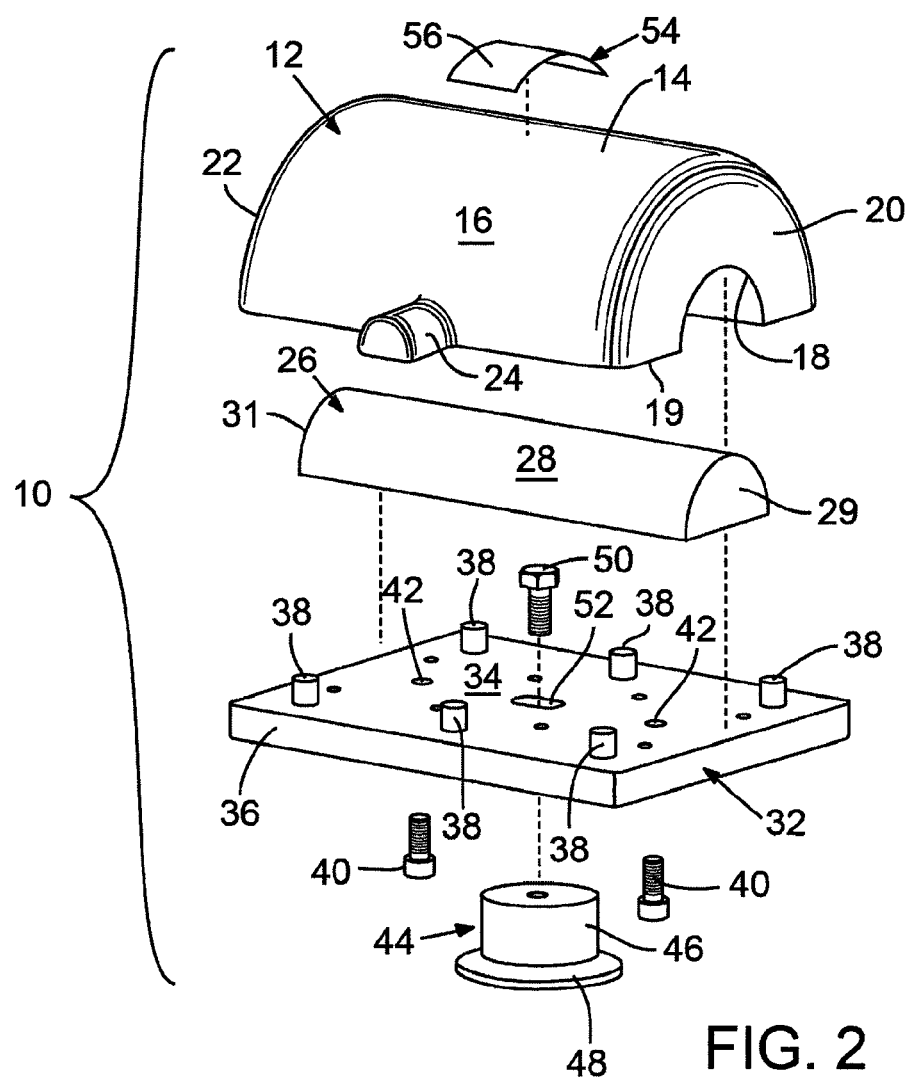
FIG. 2 is an exploded perspective view of the mount assembly of FIG. 1.
Figure 3:
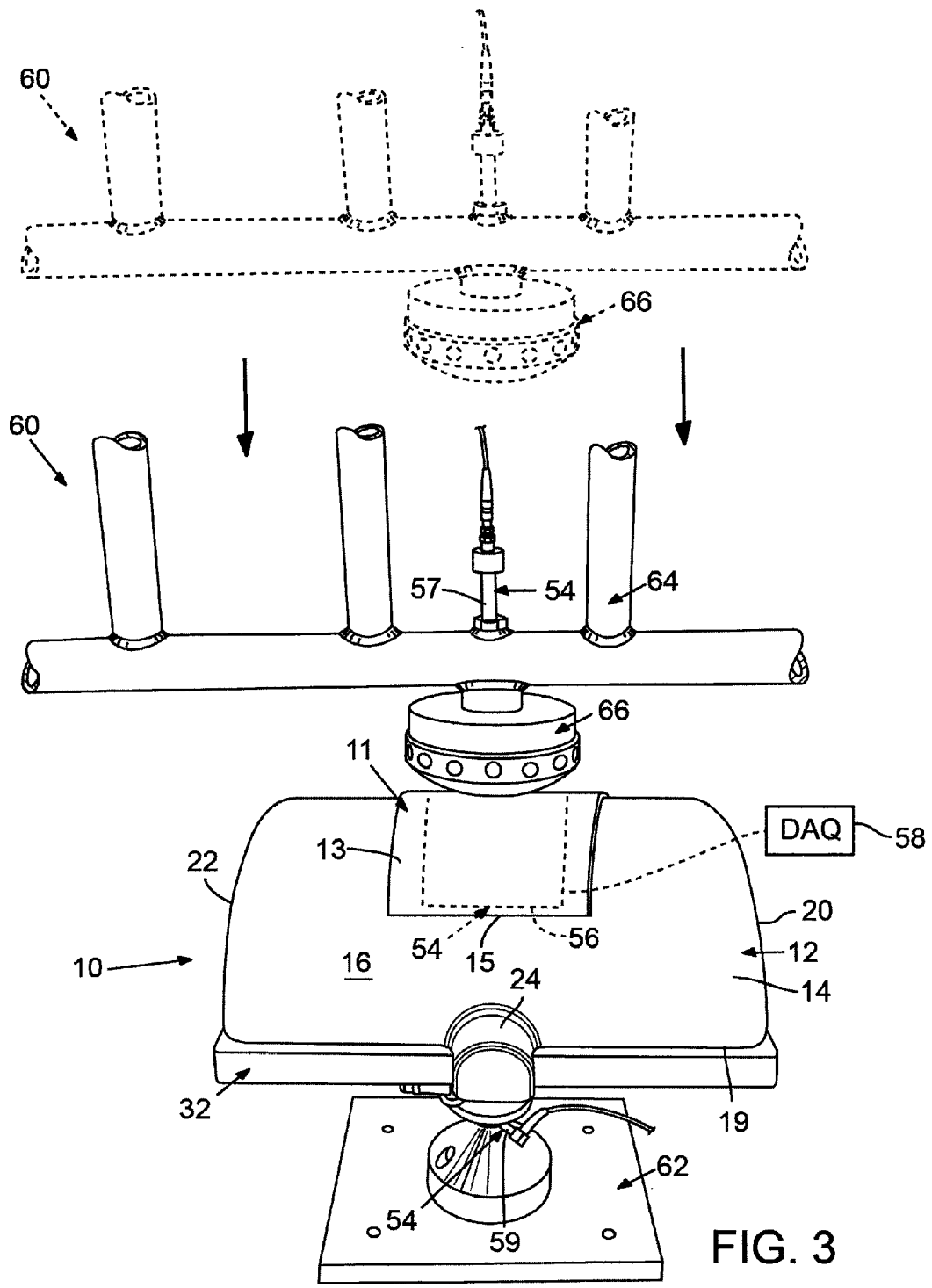
FIG. 3 is a perspective view of the mount assembly of FIG. 1 shown during an exemplary impact test of protective equipment.

Referring initially to FIGS. 1-3, a mount assembly 10 is illustrated. As will be discussed, the mount assembly 10 can be used for compression testing of an article of apparel 11 (FIG. 3). It will be appreciated that the term "compression testing" is defined broadly herein to include tests in which compression is applied to the apparel 11 for relatively large amounts of time (e.g., pressing and holding the apparel 11 under compressive loads for one or more seconds) and to include tests in which compression is applied for relatively small amounts of time (e.g., impact testing wherein compressive loads are applied to the apparel 11 nearly instantaneously).

The mount assembly 10 can be used for testing any suitable article of apparel 11. For instance, the apparel 11 can be protective apparel (i.e., wearable protective equipment), such as a thigh guard for an athlete (e.g., an American football player), or other type. As such, data can be gathered regarding how the article of apparel 11 will perform when worn during sporting or other activities.

Also, as will be discussed, the mount assembly 10 can perform under impact or other compressive loads in a manner that simulates an anatomical body part of the wearer of the apparel 11. For instance, the mount assembly 10 can simulate a thigh (i.e., an upper leg between the knee and hip joints) of a wearer such that the mount assembly 10 is configured as an "artificial thigh." Thus, as will be discussed in detail, the assembly 10 can include a core member 26 that simulates an anatomical femur bone, and the assembly 10 can include a resilient member 12 that simulates the anatomical soft tissue (e.g., skin, musculature, connective tissue, etc.) surrounding a femur. Accordingly, the mount assembly 10 can increase the accuracy of impact or other compression testing so that researchers can better evaluate the characteristics of the article of apparel 11.

As will be discussed, the resilient member 12 and core member 26 of the mount assembly 10 can be shaped similar to an anatomical thigh (more specifically, an anterior half of the thigh skin, muscles and other soft tissue as well as the anterior half of the femur). Also, the members 12, 26 of the mount assembly 10 can also have mechanical characteristics (e.g., modulus of elasticity, compression characteristics, resiliency, elasticity, durometer, resistance to resilient deformation, etc.) that are similar to the corresponding parts of an anatomical thigh. However, the mount assembly 10 of the present disclosure can be shaped and/or can be configured to exhibit the characteristics of any other anatomical body part without departing from the scope of the present disclosure. For instance, the mount assembly 10 can be configured to simulate a shoulder, a lower leg, a lower back, the buttocks, or other body part.

Still further, the mount assembly 10 will be discussed as being configured for impact testing the article of apparel 11 and for evaluating the protection provided by the apparel 11 for the wearer's body. However, as mentioned above, the mount assembly 10 could be configured for any type of other type of compression testing. The mount assembly 10 could also be configured for other testing, such as vibration testing, etc.

In the exemplary embodiments shown, the resilient member 12 can be a unitary body (i.e., monolithic) of material. The resilient member 12 can include a main body 14 that has a generally C-shaped cross section and that extends along a straight longitudinal axis X (FIG. 1). The main body 14 can also include a convex outer surface 16. The outer surface 16 can have a radius (measured from the axis X) that is substantially constant along its entire length along the axis X. In the embodiments shown, the outer surface 16 is curved about the axis X only and is only convexly curved. However, the outer surface 16 could be more complexly curved (e.g., about multiple axes, convex and concavely curved, etc.). Also, the outer surface 16 could be flat in certain areas. Additionally, the radius of the outer surface 16 can vary along the axis X (e.g., such that the outer surface 16 tapers along the axis X, similar to an anatomical thigh, etc.).

The outer surface 16 can be configured to support the article of apparel 11 thereon as shown in FIG. 3. Therefore, the outer surface 16 can be shaped in a way that corresponds and/or is substantially complimentary to that of the article of apparel 11. For instance, as shown in FIG. 3, the article of apparel 11 can include an inner surface 13 and an outer surface 15. The inner surface 13 is concave and worn against the thigh of the wearer; therefore, the outer surface 16 of the main body 14 can be convex and can have a radius that substantially matches or otherwise compliments that of the inner surface 13 to substantially simulate the fit of the article of apparel 11 to the wearer's thigh. Stated differently, the outer surface 16 of the resilient member 12 can be configured to nestingly receive and fit to the inner surface 13 of the article of apparel 11.

The main body 14 can further include a concave inner surface 18 that also has a radius that is substantially constant along its entire length. The radial distance between the inner surface 18 and the outer surface 16 (i.e., the thickness of the main body 14) can be of any suitable value. Moreover, the main body 14 can have a substantially flat first end 20 and a substantially flat second end 22. The ends 20, 22 can be substantially perpendicular to the axis X. The length of the main body 14 defined between the first and second ends 20, 22 can have any suitable value. Moreover, the main body 14 can have a substantially flat bottom surface 19 that is bisected by the concave inner surface 18.

The resilient member 12 can further include at least one projection 24. The projection 24 can have a D-shaped cross section and can project transversely away from the longitudinal axis X and away from the main body 14. In the embodiments illustrated, the projection 24 projects perpendicularly away from the axis X, but the projection 24 could project away from the axis X at any suitable angle. Furthermore, the projection 24 could curve longitudinally in some embodiments. Also, although only one projection 24 is illustrated in FIGS. 1-3, it will be appreciated that another projection 24 can project away from the opposite side of the main body 14. Moreover, the resilient member 12 could include any number of projections 24 at any suitable location without departing from the scope of the present disclosure. As will be discussed, the projection 24 can be configured for mounting the apparel 11 or for any suitable purpose.

The resilient member 12 can be made out of any suitable material. For instance, the resilient member 12 can include silicone material or other elastomeric material that is molded in any suitable molding process. As such, as will be discussed in detail, impact testing can cause the resilient member to resiliently deform from the neutral state shown in FIGS. 1-3.

Further, the core member 26 can be substantially rigid. The core member 26 can be made out of or can otherwise include a substantially rigid material, such as steel, aluminum, ceramic material, etc. The core member 26 can have a D-shaped cross section that extends along the axis X. The core member 26 can include a convex upper surface 28 and a substantially flat bottom surface 30. The core member 26 can also include a substantially flat first end 29 and a substantially flat second end 31. The first and second ends 29, 31 can be substantially perpendicular to the axis X.

The resilient member 12 can receive the core member 26 such that the resilient member 12 arcs around the core member 26 and such that the inner surface 18 of the main body 14 abuts the upper surface 28 of the core member 26. The core member 26 can be substantially coaxial with the resilient member 12. The resilient member 12 and the core member 26 can, together, have a semi-circular cross section. In the embodiments illustrated, for example, the resilient member 12 and core member 26 can cooperate to define approximately 50% of a circular cross section (i.e., span 180 degrees) to correspond to an anterior section of the thigh. However, the cross section could be configured to resemble that of the entire (i.e., anterior and posterior) thigh or other desired body part.

Additionally, the mount assembly 10 can include a base plate 32. The base plate 32 can be substantially flat and can have any suitable thickness. The base plate 32 can include an upper surface 34 and a lower surface 36. The base plate 32 can be used to support the resilient member 12 and the core member 26. Thus, the upper surface 34 can abut both the bottom surface 30 of the core member 26 and the bottom surface 19 of the main body 14 of the resilient member 12. Also, a plurality of alignment pins 38 or other fastening elements can extend into both the base plate 32 and the resilient member 12 through the upper surface 34 and the bottom surface 19, respectively. Similarly, a plurality of fasteners 40 (e.g., bolts) can fasten to both the core member 26 and the base plate 32 (e.g., via corresponding through-holes 52 defined in the base plate 32).

Also, the base plate 32 can be used to attach the mount assembly 10 to an impact testing machine 60 (FIG. 3). For instance, a mount 44 can be included that includes a cylindrical stem 46 and a radially projecting lower flange 48. A fastener 50 (e.g., a bolt, etc.) can extend through a through-hole 52 to fasten to the stem 46. The stem 46 and flange 48 can be received and fixed within a complementary opening in a frame of the impact testing machine 60 (FIG. 3).

In some embodiments, the core member 26 and the base plate 32 can be used to partially form the resilient member 12. For instance, the core member 26 and base plate 32 can be attached together and placed over a mold or trough (not shown) that has a cavity with an inner surface corresponding in shape to the outer surface 16 of the resilient member 12. Then, flowable elastomeric material (e.g., silicone) can be introduced into the cavity and cured. Thus, the outer surface 16 of the resilient member 12 can be molded and shaped against the inner surface of the cavity of the mold, the inner surface 18 can be molded and shaped against the upper surface 28 of the core member 26, and the bottom surface 19 can be molded and shaped against the upper surface 34 of the base plate 32. As such, the resilient member 12 can fit closely and can conform to the shape of the core member 26 and the base plate 32.

Still further, the mount assembly 10 can include one or more sensors 54, which is operably connected to a data acquisition device 58 (DAQ). The sensor 54 can be operable for detecting the effects of impacting or otherwise compressing the apparel 11, the resilient member 12, and/or the core member 26 during impact testing. The sensor 54 can be configured for detecting any effect of impacting or otherwise compressing the apparel 11 against the resilient member 12 (e.g., dynamic pressure, force, acceleration, impact energy, etc.). For instance, in some embodiments, the sensor 54 can be a pressure transducer 56 of a known type that detects how pressure is distributed generally across the outer surface 16 of the resilient member 12 (i.e., the pressure transducer 56 can detect a so-called "pressure map" across the outer surface 16). The pressure transducer 56 can be operable for detecting temporal, local, peak, and spatial pressures on the outer surface 16 of the resilient member 12. The pressure transducer 56 can also be operable to detect how the pressure on the outer surface 16 changes over time (e.g., during initial compression and deformation through resilient recovery of the resilient member 12).

Also, the pressure transducer 56 can be a thin, flexible sheet or film-type of transducer. The pressure transducer 56 can be disposed between the inner surface 13 of the article of apparel 11 and the outer surface 16 of the resilient member 12. It will be appreciated, however, that the transducer 56 could be configured for detecting other load data in addition to or other than pressure data. Also, the transducer 56 could be disposed anywhere with respect to the mount assembly 10 for obtaining and detecting the desired impact loading behavior of the mount assembly 10.

The pressure transducer 56 can be in communication with the DAQ 58 via a hardwired or wireless communication. The DAQ 58 can be embodied on a computer, such as a desktop computer, laptop computer, tablet, etc. The DAQ 58 can include known software, programmed logic, hardware, etc. for receiving data from the pressure transducer 56, processing the data, and outputting the data for the user. For instance, the DAQ 58 can be used to display the data graphically on a monitor or other display, the DAQ 58 can output hardcopies of the data on a printer, etc.

Thus, the mount assembly 10 can be used for impact testing or other compression testing of the article of apparel. In the case of impact testing, the mount assembly 10 can be mounted or otherwise attached to an impact testing machine 60, an example of which is partially shown in FIG. 3. The impact testing machine 60 can be a commercially available machine, such as the TWIN WIRE™ Impact Testing machine available from Cadex, Inc. of Quebec, Canada. As shown in FIG. 3, the machine 60 can include a base 62 (i.e., anvil). The stem 46 and lower flange 48 of the mount assembly 10 can be connected to the base 62 to be fixed in a stationary position. The machine 60 can further include a carriage 64 that is disposed above the mount assembly 10 and the base 62. The carriage 64 can include interconnected vertical and horizontal tubes or bars, and a head, such as an impactor 66, can be fixed to the carriage 64 and can be suspended therefrom.

One or more sensors 54 can also be attached to the carriage 64 and/or the base 62. For instance, in the embodiments illustrated in FIG. 3, an accelerometer 57 can be operatively connected to the carriage 64 for detecting accelerations during testing as will be discussed. Also, in the embodiments illustrated, a force transducer 59 can be operatively connected to the base 62 for detecting an impact force as will be discussed. Both the accelerometer 57 and force transducer 59 can be in communication with the DAQ 58 for transmitting respective data thereto.

The carriage 64 and impactor 66 can move vertically as a unit toward and away from the base 62. The carriage 64 and impactor 66 are shown in broken lines in a starting or "raised position" in FIG. 3, and the carriage 64 and impactor 66 are shown in solid lines in a final or "lowered position" in FIG. 3. It will be appreciated that the carriage 64 and impactor 66 are spaced from the apparel 11 when in the raised position, and the impactor 66 is in contact with the apparel 11 when in the lowered position.

Thus, assuming that the carriage 64 and impactor 66 are in the raised position, the mount assembly 10 is attached to the base 62 of the machine 60, and the article of apparel 11 is mounted atop the resilient member 12 below the impactor 66, an impact test can be conducted. For instance, the carriage 64 can be released such that the carriage 64 and impactor 66 freely fall toward the article of apparel 11 due to gravity. Also, in some embodiments, the carriage 64 and impactor 66 can be forcibly driven toward the article of apparel 11. When the impactor 66 impacts the apparel 11, the sensor(s) 54 can detect the effects of the impact. Specifically, the pressure transducer 56 can detect the distribution of pressure on the resilient member 12, the accelerometer 57 can detect the acceleration and deceleration of the impactor 66, and the force transducer 59 can detect the forces due to impact. The sensors 54 can transmit respective data to the DAQ 58, which can consequently gather, process, and output data corresponding to the impact effects on the apparel 11 and the mount assembly 10.

It will be appreciated that the machine 60 could operate or could be configured differently without departing from the scope of the present disclosure. For instance, the machine 60 could include a carriage 64 that swings or otherwise rotates about an axis to impact the apparel 11. Also, the machine 60 could actively drive the impactor 66 toward the apparel 11 in some embodiments. Moreover, the carriage 64 could be configured to reciprocate between the raised and lowered positions to repeatedly impact the apparel 11. Also, in some embodiments, the apparel 11 could be substantially centered over the longitudinal axis X of the mount assembly 10 and the impactor 66 could be configured to travel along a vector that intersects the axis X; however, the apparel 11 and/or the mounting assembly 10 could be disposed relative to the impactor 66 such that the vector of travel of the impactor 66 is spaced away from the axis X of the mount assembly 10. In these embodiments, the testing could be configured for simulating glancing blows on the apparel 11, for detecting shear loads on the resilient member 12, etc.

Also, the testing parameters can be varied. For instance, the impactor 66 can be interchangeable with impactors 66 of different weights. Thus, if a lighter impactor 66 is used, there can be less impact energy when impacting the apparel 11. On the contrary, if a heavier impactor 66 is used, there can be more impact energy. Also, the impactor 66 can be interchangeable with impactors 66 of different shapes and sizes. For instance, the bulbous impactor 66 shown in FIG. 3 could be replaced by a wedge-shaped or tapered impactor 66 or an impactor 66 of another shape. Thus, the area of contact between the impactor 66 and the apparel 11 can be changed to thereby change the impact energy. Additionally, the stroke of the impactor 66 (i.e., the linear distance from its raised position to its lowered position) can be selectively varied to thereby vary the impact energy delivered by the impactor 66 to the apparel 11.

Figure 4:
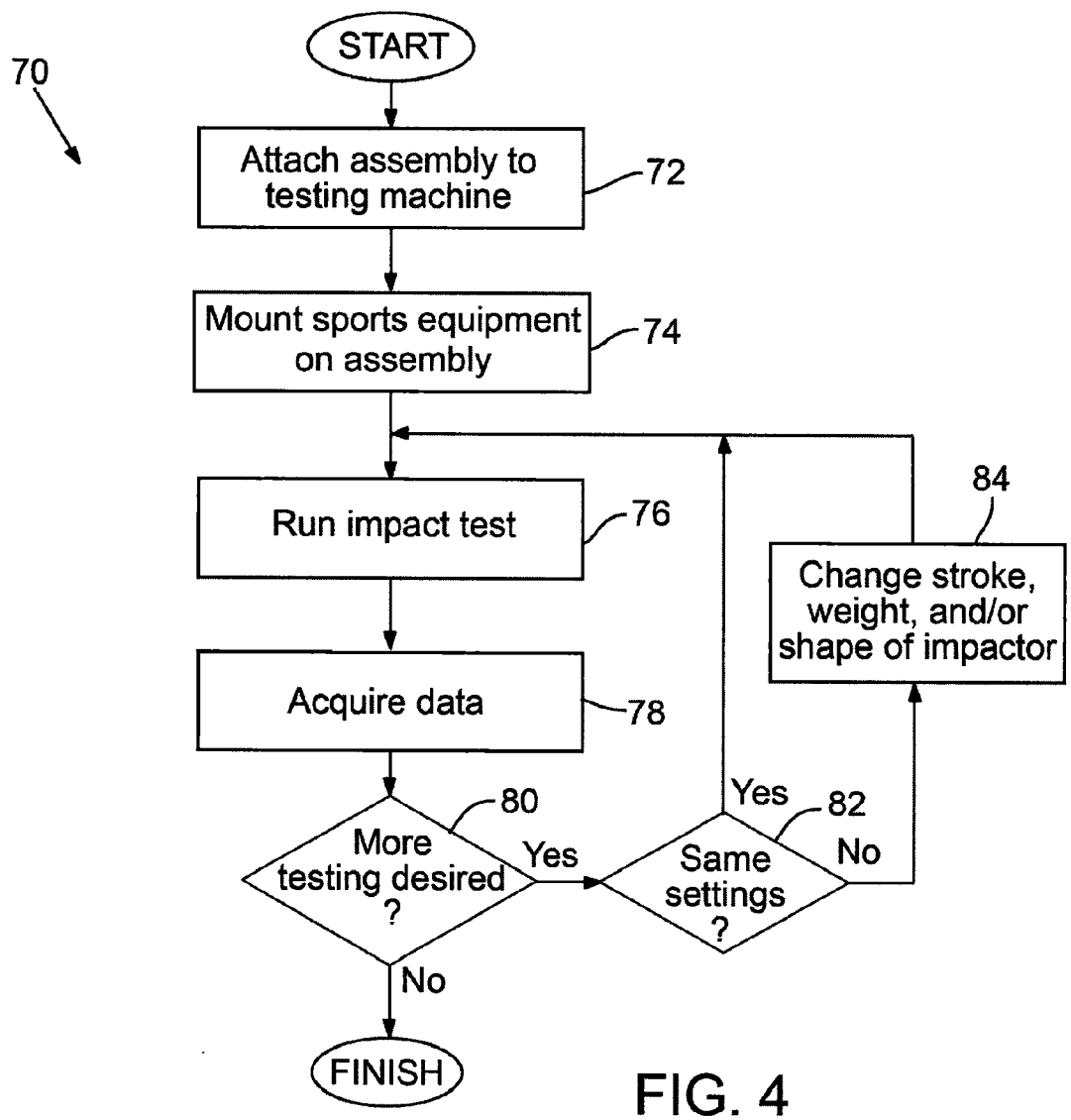
FIG. 4 is a flowchart of various exemplary embodiments of a method of impact testing using the mount assembly of FIG. 1.

Referring now to FIG. 4, a method 70 of impact testing the article of apparel 11 using the mount assembly 10 is illustrated according to various exemplary embodiments. As shown, the method 70 can begin in block 72, wherein the mount assembly 10 (identified as an "artificial thigh" in FIG. 4) is mounted on the impact testing machine 60. Then, in block 74, the article of apparel 11 (identified as a "thigh guard" in FIG. 4) can be mounted onto the outer surface 16 of the resilient member 12. In some embodiments, the apparel 11 can be simply supported on the outer surface 16 without additional straps, fasteners, or other similar devices. However, in other embodiments, straps, fasteners, or other devices can extend from the apparel 11 and can secure to one of the projections 24 to substantially fix the apparel 11 to the resilient member 12.

Next, in block 76, the user can run the impact test 76. As described above, the carriage 64 and impactor 66 can drop toward the apparel 11 such that the impactor 66 impacts the apparel 11. Then, in block 78, the impact effects (e.g., pressure distribution on the outer surface 15 during the impact, accelerations, decelerations, impact forces, etc.) can be detected by the sensors 54, and corresponding data can be processed and output by the DAQ 58.

Next, in decision block 80, it can be determined whether more testing is required. For instance, the user may want to collect load data from several tests to increase the accuracy of the results. Also, the user may want to run the impact test several times using different test parameters. If testing is complete (i.e., block 80 answered negatively), then the method 70 can finish. However, if more testing is desired (i.e., block 80 answered positively), then decision block 82 can follow.

In block 82, the user can determine whether the test settings (i.e., test parameters) should remain the same as in the previous test. If the settings are to remain the same (i.e., block 82 answered positively), then the method 70 can loop back to block 76. However, if the test settings are to be varied (i.e., block 82 answered negatively), then block 84 can follow.

In block 84, the user can reconfigure the testing machine 60 such that the apparel 11 and mount assembly 10 are subject to different impact energy from the impactor 66. For instance, as mentioned above, the impactor 66 used in the previous test can be interchanged with another impactor 66 of different weight and/or shape. Alternatively or in addition to these changes, the stroke of the carriage 64 and impactor 66 can be varied. More specifically, the initial, raised position of the carriage 64 (and, thus, the amount of travel of the impactor 66 during the test) can be adjusted to be closer or farther away from the apparel 11 as compared with the previous test. Then, the method 70 can loop back to block 76.

Accordingly, the testing method 70 can be run one or more times to obtain information about how the apparel 11 and mount assembly 10 perform when subjected to impact from the impactor 66. Since the mount assembly 10 is configured to simulate the anatomy (here, an anatomical thigh), the test data can be used to discover how well the apparel 11 protects a person's body during sporting activities, etc. Testing can be conducted to simulate real-world impact conditions such that the data can be very accurate. Accordingly, the apparel 11 can be designed, configured, and tested to better protect the wearer's body.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A mount assembly for compression testing of an article of apparel on a compression testing machine having a head and a sensor, the mount assembly comprising:
   a substantially rigid core member; and
   a resilient member including a main body with an inner surface that abuts the substantially rigid core member, the resilient member being supported on and at least partially covering the substantially rigid core member, the resilient member including at least one projection extending away from the substantially rigid core member and the main body, the resilient member being configured to support the article of apparel thereon, the resilient member being configured to resiliently deform in response to a compression applied to the article of apparel from the head of the compression testing machine such that the sensor detects an effect of the compression on at least one of the resilient member and the core member.

2. The mount assembly of claim 1, further comprising the sensor, wherein the sensor includes a pressure transducer that is operable to detect a pressure on at least one of the resilient member and the core member due to the compression applied to the article of apparel.

3. The mount assembly of claim 2, wherein the pressure transducer is operable to detect a pressure on the resilient member due to the compression applied to the article of apparel.

4. The mount assembly of claim 3, wherein the pressure transducer is disposed between the article of apparel and an outer surface of the resilient member.

5. The mount assembly of claim 1, wherein the resilient member is configured to simulate resilient deformation of anatomical soft tissue due to compression.

6. The mount assembly of claim 1, wherein the resilient member includes an elastomeric material.

7. The mount assembly of claim 6, wherein the elastomeric material is silicone.

8. The mount assembly of claim 1, wherein the resilient member includes an outer surface that is convexly curved, the outer surface configured to support the article of apparel.

9. The mount assembly of claim 8, wherein the outer surface is configured to nestingly receive the article of apparel.

10. The mount assembly of claim 9, wherein the article of apparel is a protective article of apparel that is configured to protect an anatomical thigh.

11. The mount assembly of claim 1, further comprising a base plate that supports the core member and the resilient member thereon.

12. The mount assembly of claim 11, wherein both the core member and the resilient member abut the base plate.

13. The mount assembly of claim 1, further comprising the sensor, wherein the sensor is operable to detect an effect of an impact applied to the article of apparel from the head on at least one of the resilient member and the core member.

14. A method of compression testing an article of apparel comprising:
mounting the article of apparel on a resilient member that is supported by a substantially rigid core member;
applying a compression to the article of apparel with a head by impacting the article of apparel with the head at an impact energy;
detecting an effect of the compression on at least one of the resilient member and the rigid core member, and
repeating the impacting of the article of apparel to vary the impact energy, wherein repeating the impacting of the article of apparel to vary the impact energy includes varying one or more of a stroke distance of the head, a weight of the head, and a shape of the head.

15. The method of claim 14, wherein mounting the article of apparel includes nesting the article of apparel to a convexly curved outer surface of the resilient member.

16. The method of claim 14, further comprising providing a pressure transducer between the article of apparel and an outer surface of the resilient member, and wherein detecting an effect of the compression on at least one of the resilient member includes detecting a pressure distribution on the resilient member due to the compression using the pressure transducer.

17. An artificial thigh for impact testing of a thigh guard on an impact testing machine having an impactor head, the artificial thigh comprising:
a single-body resilient member having a main body with a C-shaped cross section and that extends along a straight longitudinal axis, the main body having an outer surface configured to nestingly receive the thigh guard thereon, the main body also having an inner surface, the resilient member also including at least one projection that projects perpendicularly away from the longitudinal axis and away from the main body, the resilient member being made from silicone, the resilient member being configured to resiliently deform in response to an impact applied to the thigh guard from the impactor head of the impact testing machine;
a substantially rigid core member having a D-shaped cross section and that extends along the longitudinal axis, the core member received by the resilient member to abut against the inner surface of the resilient member and to be at least partially covered by the resilient member;
a base plate that supports the core member and the resilient member, the base plate configured to attach to the impact testing machine; and
a pressure sensor that is configured to be disposed between the thigh guard and the outer surface of the resilient member, the pressure sensor operable to detect a pressure distribution on the outer surface of the resilient member due to the impact applied to the thigh guard from the impactor head of the impact testing machine.

* * * * *